United States Patent
Menegassi De Almeida et al.

(10) Patent No.: US 12,162,826 B2
(45) Date of Patent: Dec. 10, 2024

(54) PROCESS FOR PRODUCING A RENEWABLE ISOPARAFFIN COMPOUND, RENEWABLE ISOPARAFFIN COMPOUND AND USE OF THE RENEWABLE ISOPRAFFIN COMPOUND

(71) Applicant: PETROLEAO BRASILEIRO S.A.—PETROBAS, Rio de Janeiro (BR)

(72) Inventors: Rafael Menegassi De Almeida, Rio de Janeiro (BR); Marlito Gomes Junior, Petropolis (BR); Edimilson Jesus De Oliveira, Niteroi (BR); Carlos Rene Klotz Rabello, Rio de Janeiro (BR); Anderson Rouge Dos Santos, Duque de Caxias (BR)

(73) Assignee: Petroleo Brasileiro S.A.—Petrobras, Rio de Janeiro (BR)

( * ) Notice: Subject to any disclaimer, the term of this patent is extended or adjusted under 35 U.S.C. 154(b) by 659 days.

(21) Appl. No.: 17/291,045

(22) PCT Filed: Nov. 5, 2019

(86) PCT No.: PCT/BR2019/050479
§ 371 (c)(1),
(2) Date: May 4, 2021

(87) PCT Pub. No.: WO2020/093127
PCT Pub. Date: May 14, 2020

(65) Prior Publication Data
US 2021/0371366 A1 Dec. 2, 2021

(30) Foreign Application Priority Data
Nov. 7, 2018 (BR) .......................... 102018072896-2

(51) Int. Cl.
*C07C 41/09* (2006.01)
*C07C 1/22* (2006.01)
(Continued)

(52) U.S. Cl.
CPC ................. *C07C 41/09* (2013.01); *C07C 1/22* (2013.01); *C07C 1/24* (2013.01); *C07C 29/34* (2013.01); *C10L 1/06* (2013.01); *C07C 2523/755* (2013.01)

(58) Field of Classification Search
CPC ....... C07C 1/22; C07C 1/24; C07C 2523/755; C07C 29/34; C07C 41/09; C07C 9/16;
(Continued)

(56) References Cited

U.S. PATENT DOCUMENTS 5,326,925 A 7/1994 Sachtler

FOREIGN PATENT DOCUMENTS

| CN | 101811920 A | * | 8/2010 |
| CN | 105384593 A | * | 3/2016 |

(Continued)

OTHER PUBLICATIONS

CN-105384593-A English Translation (2016).*
(Continued)

*Primary Examiner* — Ellen M McAvoy
*Assistant Examiner* — Chantel Graham
(74) *Attorney, Agent, or Firm* — RAPHAEL BELLUM PLLC

(57) ABSTRACT

The present invention refers to a process for producing a renewable isoparaffin compound with a high octane rating, comprising a step of Guerbet reaction between an initial C5 alcohol charge obtained from renewable raw material and methanol to produce a branched renewable C6 alcohol; dewatering of the branched renewable C6 alcohol into a C6 olefin; and hydrogenation of the C6 olefin into renewable (Continued)

isoparaffin. A renewable isoparaffin compound with a high octane rating, comprising at least 50% carbon of renewable natural origin in its composition, and use of said renewable paraffin in gasolines in general and in special high-performance gasolines, such as aviation gasoline, are also described.

20 Claims, 2 Drawing Sheets

(51) Int. Cl.
*C07C 1/24* (2006.01)
*C07C 29/34* (2006.01)
*C10L 1/06* (2006.01)

(58) Field of Classification Search
CPC ....... C07C 11/107; C07C 31/125; C07C 5/03; C10L 1/06; C10G 2300/1011; C10G 2300/305; C10G 2400/02; C10G 3/42; C10G 3/50; C10G 45/00; Y02P 30/20
See application file for complete search history.

(56) References Cited

FOREIGN PATENT DOCUMENTS

| EP | 2913319 A1 * | 9/2015 | .............. B01J 23/40 |
| EP | 2585421 B1 * | 9/2018 | ............ B01J 21/066 |

OTHER PUBLICATIONS

CN-101811920-A English Translation (2010).*
English Translation of International Search Report in International Application No. PCT/BR2019/050479, dated Dec. 13, 2019.

* cited by examiner

PROCESS FOR PRODUCING A RENEWABLE ISOPARAFFIN COMPOUND, RENEWABLE ISOPARAFFIN COMPOUND AND USE OF THE RENEWABLE ISOPRAFFIN COMPOUND

FIELD OF INVENTION

The present invention refers to a process for obtaining a gasoline having increased renewable content, specifically to a process for producing a high octane renewable isoparaffin compound and use thereof in Otto cycle engines.

BACKGROUND OF THE INVENTION

There is a need in the art for obtaining high octane, non-oxygenated, renewable components for compounding gasoline.

Despite the wide use of ethanol, from the fermentation of sugar cane, as a component of the gasoline employed in Otto cycle engines, there is a need for obtaining other renewable components since the oxygen content in ethanol can have drawbacks.

Airplanes having piston engines operate under high compression ratio conditions, including compression of air admitted to the engine, prior to mixing with the fuel (by turbo-compression or supercharging). In this way, aviation gasoline should have high octane in order to withstand the engine operating conditions without premature detonation. As there are limitations to the use of additives for increasing octane (for example: tetraethyl lead), the high octane should result from gasoline compounding (high octane components).

Yet for aviation fuels, there is a tendency to replace fossil components with renewable components. Several nations signing Paris Agreement, set By UNO on Nov. 4, 2016, have agreed upon the decrease in emissions from non-renewable source and compensation of emissions by carbon credits.

The ethanol, by having high octane, can be used as a component in aviation gasoline. However, the high oxygen content of the molecule (42% by mass), substantially decreases the heating power. This feature, undesirable by limiting flight management, restricts the percentage of ethanol in the final composition of aviation gasoline.

Thus, there is a need to obtain high octane, renewable streams, mainly high octane renewable isoparaffins, since isoparaffins have the highest heat capacity per unit mass than aromatics and naphthenic.

Gasoline is a product obtained from petroleum refining and the composition thereof depends on its use, automotive or aviation, from its origin and from the oil refining processes.

Aviation gasoline is typically a mixture of hydrocarbons having 4 to 10 carbon atoms, which distills between approximately 30° C. and 170° C. and is obtained by processes developed for producing high octane compounds, such as, but not limited to: alkylation of isoparaffin with olefin; catalytic reforming and dimerization of isobutene, followed by hydrogenation. Automotive gasoline, in turn, is a mixture of hydrocarbons containing from 4 to 12 carbon atoms, having boiling points between 30° C. and 225° C. Based on their octane number, automotive gasolines are generally classified into two types: "regular" and "premium" (higher octane).

The annual sale of regular automotive gasoline (type C) in Brazil has reached 44 million m³, in 2017, while that of aviation gasoline has passed from 50 thousand m³ (2008) to almost 80 thousand m³ (2017), according to data from statistical annual record of 2018 of ANP.

Due to the importance of fuels for Otto Cycle engines, several efforts are being carried out in order to ensure quality thereof and to minimize the environmental effects of their use and possible health damage to the population. This is especially important for the development of high octane, renewable source components for producing tetraethyl lead-free aviation gasoline.

The use of renewable source compounds in the formulation of "premium" gasolines, special competition gasolines (for example, for Formula 1) or aviation gasoline, is limited due to the octane specification. The oxygen content of ethanol makes its use restricted to regular and "premium" gasolines, since addition thereof reduces the heating power of the fuel, making the supplies more frequent, which is undesirable for competition and aviation gasolines.

As an example of special competition gasoline, we can cite the competition gasoline of F1 (FIA-Federation Internationale de L'Automobile, http://www.fia.com/regulation/category/110), which should be in accordance with the following constraints:

Limitation of the amount of gasoline to no more than 100 kg per race, being preferred components with the highest possible heat capacity per unit mass (MJ/kg).

Renewable compounds of at least 5.75% by weight.

Reid Vapor Pressure (PVR) of 45 to 60 kPa (method EN13016-1).

Olefin content not greater than 17% by weight.

Isoamyl alcohol can be obtained from a renewable source, being the major constituent of fusel oil, by-product of the sugar-to-ethanol fermentation. Typically, about 3 liters of fusel oil are produced for each m³ of ethanol produced and can reach 4-8 liters when microbiological production is inhibited. In Brazil there were produced almost 30 million m³ ethanol, in 2017, corresponding to 90,000 m³ fusel oil.

An example of a hydrocarbon of renewable origin are isopentanes that can be obtained by dewatering of isoamylic alcohol.

However, pentenes have limited use due to the high PVR. High PVR also limits its use in aviation gasoline since, with altitude the evaporation of lighter compounds increases. Compounds in the range $C_6$ or higher are desirable in these cases.

The present invention refers to obtaining renewable $C_6$ compounds.

Further, there is a limitation on the use of olefins and aromatics in Otto cycle engines in general, either by environmental and health issues (aromatics) and fuel stability, being preferred components higher octane isoparaffins. Among the C6-paraffins, the one of highest octane is 2,3-dimethyl-butane, having 101 of RON Octane and 94.3 MON octane.

Few routes are known in the art for producing compounds in the range of $C_6$ or higher. There are biotechnological processes of fermentation for producing renewable $C_4$, which can be oligimerized by acid catalysis known in the art, producing $C_8$. However, $C_8$ can be very heavy for high-speed engines such as Formula 1 or aviation, limiting application thereof. Other technologies, such as hydrogenolysis of sugars, produce hydrocarbons of few branching.

There are documents in the art that teach the production of gasoline from renewable sources. U.S. Pat. No. 3,324,438 B2 discloses a process for producing aviation gasoline or kerosene by mixing with at least one paraffin-rich component and one component rich in cyclic compounds, wherein each of the components is generated from a renewable raw material.

The paraffin-rich component is generated from glycerides and fatty acids free from raw materials such as vegetable and animal oils. The cyclic-rich component is generated from biomass derived pyrolysis oil. The source of the animal or vegetable oil and the biomass can be the same renewable source.

The preparation of the paraffins-rich component involves hydrogenation, decarboxylation, decarbonylation and/or hydrodeoxygenation steps of renewable raw materials. The preparation of the cyclic-rich component is made through a first deoxygenation step where the pyrolysis oil is partially deoxygenated. Next, after the separation of water, gases and light hydrocarbons, the stream proceeds to a second deoxygenation step in which a cyclic hydrocarbon stream is generated to be used in the production of the fuel.

In addition, the patent document CA2951614 A1 describes a process for producing a high octane component from the co-processing of vacuum gas oil and a feedstock of renewable origin in catalytic cracking units.

However, these documents teach long, complex, and difficult to implement processes for producing renewable gasoline.

As will be further detailed below, the present invention provides solution to the problems of the prior art described above, in a practical and efficient manner, by a Guerbet reaction with heterogeneous catalysts for coupling C5 alcohol with methanol, resulting in C6 alcohol, which is converted into renewable C6 isoparaffin. Further, the method disclosed herein decreases the side reactions that disfavor the achievement of renewable C6 isoparaffin.

SUMMARY OF INVENTION

The present invention refers to a process for producing a high octane, renewable isoparaffin compound comprising a Guerbet reaction step between an initial charge of $C_5$ alcohol-obtained from renewable raw material- and methanol, optionally also from renewable raw material, to produce a branched renewable $C_6$ alcohol; dewatering of the branched renewable $C_6$ alcohol to $C_6$ olefin; and hydrogenating the $C_6$ olefin to renewable isoparaffin, optionally with the combined dewatering and hydrogenation of the renewable $C_6$ alcohol, obtaining renewable $C_6$ isoparaffin.

Also disclosed is a high octane, renewable isoparaffin compound comprising at least 50% carbon of renewable natural origin in the composition thereof according to ASTM D6866.

This process allows obtaining high octane C6 isoparaffin for use in gasolines in general and, preferably, in competition and aviation gasolines.

BRIEF DESCRIPTION OF FIGURES

The advantage described above is clear to those skilled in the art from the accompanying figures.

DETAILED DESCRIPTION OF THE INVENTION

Figure 1:
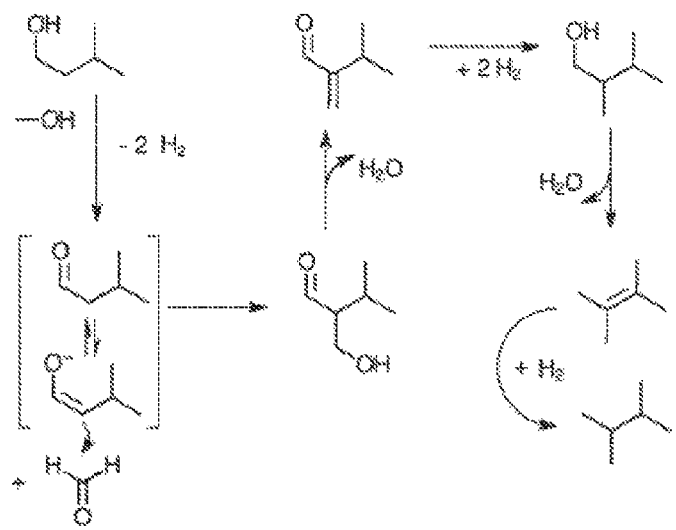
FIG. 1 shows the steps of Guerbet reaction for producing 2,3-dimethyl-butanol, from isoamyl alcohol and methanol, followed by dewatering and hydrogenation reactions.

The present invention refers to a process for producing a renewable isoparaffin compound having high octane comprising a Guerbet reaction step between an initial charge of $C_5$ alcohol obtained from renewable raw material and methanol to produce a branched renewable $C_6$ alcohol; a step of dewatering the branched renewable $C_6$ alcohol to a $C_6$ olefin; and a step of hydrogenating the $C_6$ olefin to renewable isoparaffin.

The Guerbet reaction involves the reaction of a primary and/or secondary alcohol (or mixture of alcohols), as follows:

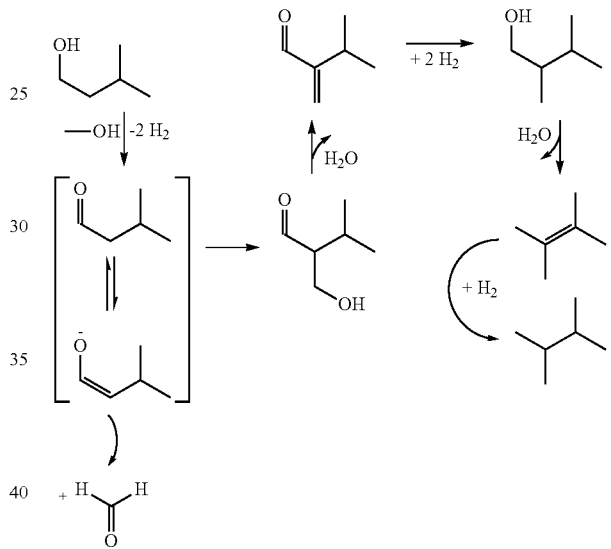

- dehydrogenation: hydroxyls dehydrogenate to carbonyls (generating 2 $H_2$), primary alcohols to aldehydes and secondary to ketones;
- aldol condensation: the aldol condensation between two molecules containing carbonyls (aldehyde or ketone), followed by water elimination;
- hydrogenation: acetone α,β-unsaturated (enone) is hydrogenated, with the original hydroxyls functioning as hydrogen donors.

After the Guerbet reaction, the resulting branched alcohol has a longer chain.

The resulting Guerbet alcohols are primary or secondary—although most alcohols produced from primary adducts also result in primary alcohols. The properties imparted by the alcohol branched structure are well appreciated: low toxicity, liquids at extremely low temperatures, low volatility, good lubricants, good oxidative stability, excellent initial color, biodegradability, among others.

In the absence of methanol, the reaction of the isoamyl alcohol (3-methyl-1-butanol) is the self-coupling, resulting in 2-isopropyl-5-methylhexanol, as scheme of the reaction below:

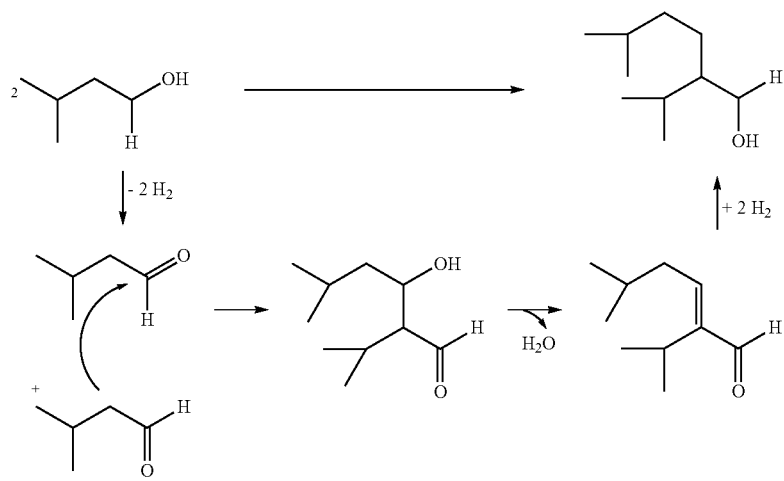

The self-condensation of the isoamyl alcohol is not of interest for gasoline, as it produces heavier compound, but it may be interesting for producing special solvents or component/additive for diesel and aviation kerosene.

In one embodiment of the invention, the process for producing a renewable isoparaffin compound comprises a step of Guerbet reaction between an initial charge of isoamyl alcohol, obtained from fusel oil, and methanol, to produce a 2,3-dimethyl-1-butanol compound: a step of dewatering of 2,3-dimethyl-1-butanol to 2,3-dimethyl-1-butene; and a hydrogenation step of 2,3-dimethyl-1-butene to 2,3-dimethyl-butane, comprising carbon of renewable origin.

In the mixture of isoamyl alcohol with methanol, the following reactions occur, depending on the amount of each compound:
- with methanol (MeOH) absent or sub stoichiometric: the coupling reaction of isoamyl alcohol with itself would be favored;
- with excess methanol (MeOH): the reaction of coupling the isoamyl alcohol with it would preferably be disfavored.

In order to make available more methanol to favor the condensation with $C_5$ alcohol, the molar ratio of methanol to $C_5$ alcohol of the present process is from 1.5:1 to 12:1, preferably from 3 to 6:1.

The isoamyl alcohol used in the initial charge preferably comprises from 50 to 100% carbon of renewable natural origin. The by-product isoamyl alcohol from sugar cane fermentation has 100% renewable source carbon.

Isopropyl alcohol yield can be increased selecting yeast strains that produce greater yield in fusel oil as a by-product of sugar cane fermentation. Further, this same yield can be increased by means of genetic engineering techniques known in the art to increase the yield in isoamyl alcohol during sugar fermentation from sugar cane. Further, the sugar from the fermentation may not be sucrose from sugar cane, but other sugar such as glucose from the hydrolysis of cellulose from the cane bagasse or starch present in corn, potato, manioc or other amylaceous plant. The source of cellulosic and sugar material can further be algae, wood industry waste, agricultural or sugar production waste, such as cane bagasse.

Preferably the Guerbet reaction catalyst comprises a heterogeneous solid, with a component of basic function and a component of hydrogenation/dehydrogenating function. Even more preferably, the residual acidity of the catalyst or support is such that secondary reactions of dewatering of the alcohols and etherification are minimized.

Alternatively, in order to make predominant the reaction of combining the isoamyl alcohol with methanol, in the Guerbet reaction, ammonia or a nitrogenous compound can be used in order to minimize the parallel reactions of dewatering of the alcohols and the formation of ethers. Preferably, the ammonia or the nitrogenous compound is added to the initial charge in a content of 0 to 5,000 ppm, more preferably from 200 to 2,500 ppm, even more preferably from 500 to 1,500 ppm.

Further, in a particular embodiment, the nitrogenous compound is ammonia. In another mode of the invention, the nitrogenous compounds or the ammonia are returned to the reactor after being separated from the reaction product.

The Guerbet reaction takes place in a reactor with heterogeneous catalyst, preferably continuous, fixed bed, more preferably in packing flow, wherein typical operating conditions are:
- temperature from 250 to 550° C., preferably 300 to 500° C., more preferably from 350 to 450° C., liquid hourly space velocity (LHSV) from 0.25 to 5 hr$^{-1}$, preferably 0.5 to 3 hr$^{-1}$, more preferably 1 to 2 hr$^{-1}$ pressure from 1 to 100 bar, preferably 5 to 100 bar, more preferably 10 to 50 bar.
- volumetric ratio $H_2$/charge: 10 to 2,000 Nl/l, preferably 100 to 1,000 Nl/l, more preferably 200 to 1,000 Nl/l.

Optionally water can be added to the reaction. Water has the effect of decreasing methanol etherification and inhibiting isoamyl alcohol dewatering reactions. It also favors separation of unreacted methanol by concentrating it in aqueous phase, while C5 and C6 alcohols and aldehydes remain in organic phase.

Higher pressures favor thermodynamically the coupling reaction of alcohols. Although the hydrogen generated in the dehydrogenation step of the Guerbet reaction is later consumed in the final hydrogenation step of Guerbet reaction, it is preferred to feed additional $H_2$. The presence of $H_2$ in the charge functions to maintain reduced catalyst metal and favor the final hydrogenation step of Guerbet reaction, as well as converting nitrogen precursors to $NH_3$.

Figure 2:
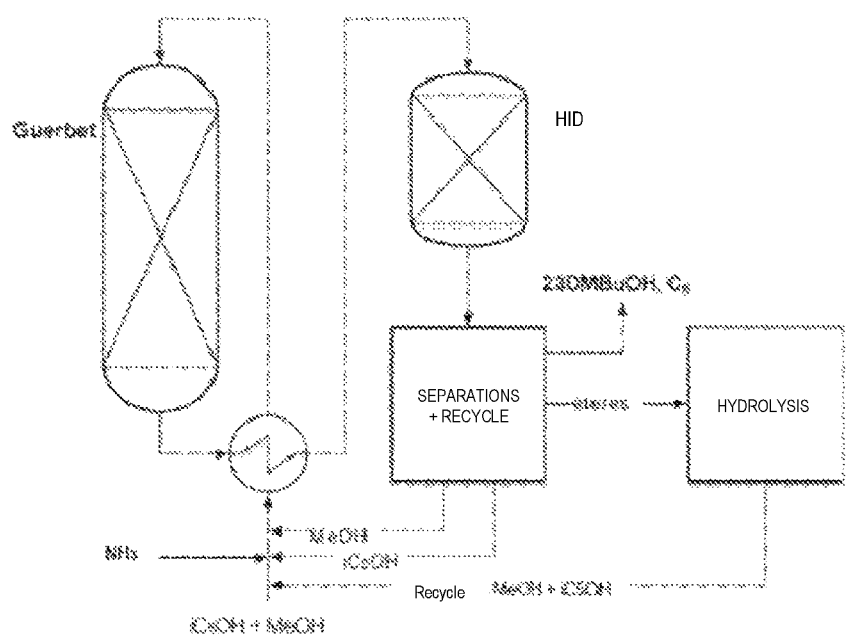
FIG. 2 shows a schematic of an embodiment of the process comprising a Guerbet reactor and a hydrogenation reactor to obtain 2,3-dimethyl-butanol, which is then dehydrated and hydrogenated to obtain 2,3-dimethyl-butane.
Figure 3:
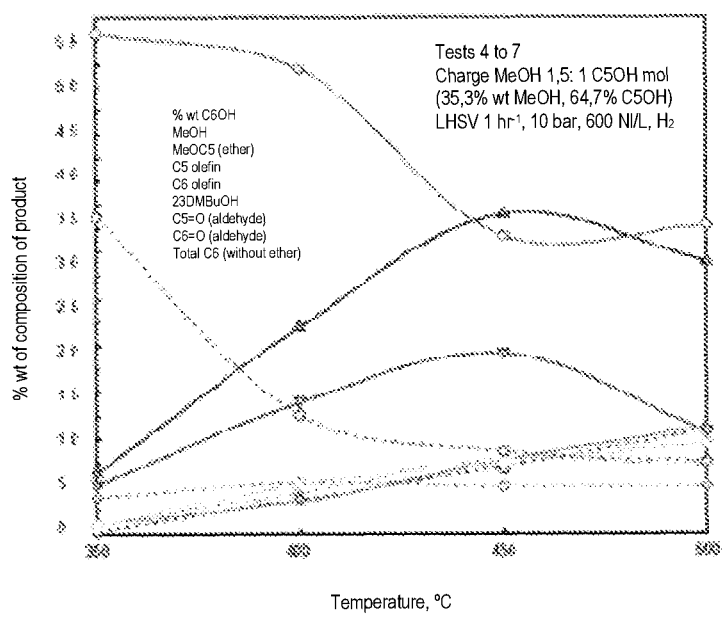
FIG. 3 shows the yields of 2,3-dimethyl-butanol as a function of reaction temperature (tests 4 to 7 conditions in Table 4).

In an alternative embodiment, according to FIG. 2, a hydrogenation reactor can be incorporated into the process, where the catalyst used, for example, of nickel (Ni), with hydrogenation function preferably at a temperature of less than 200° C., pressure between 5 and 60 bar and LHSV between 1 and 5 hr$^{-1}$, more preferably between 2 and 4 hr$^{-1}$, increases the yield of $C_6$ alcohol and regenerates $C_5$ alcohol. Other catalysts may be employed for hydrogenation, containing hydrogenating metals, not limited to Cu, Cr, Co, W, Ru, Pt, Pd.

This hydrogenation reactor can facilitate the overall separation scheme of components, converting $C_5$ aldehyde, formed by dehydrogenation of $C_6$ alcohol into the Guerbet reactor, to $C_6$ alcohol.

In either process scheme, with or without hydrogenation reactor, the process comprises a separation section, for recovering ethers, $C_5$ aldehyde and unreacted isoamyl alcohol.

The separation section can use any process for separating components known from the prior art as, for example, the distillation process.

Unreacted isopropyl alcohol and corresponding $C_5$ aldehyde or mixture of both can be sent again to Guerbet reactor. In the hydrogenation reactor the aldehydes are converted into alcohols. If the hydrogenation reactor is before the separation, preferably isoamyl alcohol will return the charge of Guerbet reactor.

The ethers are preferably sent to a hydrolysis step in order to be recycled to the initial charge as methanol and $C_5$ alcohol, as well as the methanol and $C_5$ alcohol leaving the separation section. The hydrogenation reactor, when employed, can be after the separation for recycle of methanol, unreacted isoamyl alcohol and corresponding $C_5$ aldehyde.

Among the ethers to be hydrolyzed to return to the main reactor of Guerbet reaction are methyl ether of isoamyl alcohol, dimethyl ether and ether of isoamyl alcohol and minor portions of ethers containing $C_6$ chain in the composition. For hydrolysis, water feed is needed to the hydrolysis reactor, at least in the stoichiometric ratio. The hydrolysis is easily effected by reacting the ether with water in acid catalyst, such as an acidic ion exchange resin or acid catalysts known in the art.

Alternatively, it can be performed the direct recycle of ethers or mixture of ethers remaining more alcohols to the main Guerbet reactor for hydrolysis. In this particular case it is interesting to feed $H_2O$ to the reaction charge.

Water can optionally be fed to the charge of Guerbet reactor also to not favor etherification and dewatering reactions.

Another separation process that can be employed for, for example, recovering MeOH is an extraction of the organic product with aqueous phase. The heavy alcohols remain preferably in organic phase while methanol passes to the aqueous phase. Typical amounts of water relative to the organic phase content are from 0.1 to 5 times, preferably from 0.5 to 2 times the volume of the organic phase, more preferably from a ratio of 0.1 to 1 volume of aqueous phase per organic phase by volume. The extraction may occur in only one stage of contact equilibrium, or may occur preferably countercurrent, in more than one separator. The water can be fed after the Guerbet reactor or be already present in the Guerbet reactor charge.

The separation and recovery means of methanol from the aqueous stream are known to those skilled in the art. The separation of alcohols and hydrolysis of ethers can still be combined to preferably recycle unreacted alcohols. It is known in the art the catalytic distillation with acid catalyst in distillation sections.

The bifunctional catalyst of Guerbet reaction has a basic site and a hydrogenating/dehydrogenating function.

One of the suitable catalysts is the Ni supported in MgO/Al$_2$O$_3$, with a composition of 10 to 30% Ni, 2 to 10% NiO, 50 to 70% MgO and 5 to 25% by weight Al$_2$O$_3$, wherein the catalyst is reduced between 25° and 350° C.

Another possible basic support is alumina doped with alkali and/or alkaline earth metals, such as K, Na, Ca, Cs or Rb (basic metals, such as Group I or Group II).

In addition to Ni, as hydrogenating/dehydrogenating metal, metals of Groups of Cu, Co, Fe, Zn, alone in combination may be employed. For the hydrogenating/dehydrogenating function metals od group VB, VIIB, IB, such as V, Cr, Mo, W, Fe, Ru, Co, Ni, Cu, Ag, Pt/Pd, preferably, Cu and/or Ni are used.

Several heterogeneous catalysts for Guerbet reaction are known in the art and should combine the hydrogenating/dehydrogenating function with basic function.

Basic supports to which function is added hydrogenating function are known in the art. The basic supports may be those listed, but not limited to: alumina doped with K or Ca or Mg, or hydrotalcite, or doped hydrotalcite, or MgO, or basic carbons or exchanged zeolites or other supports known in literature. Other known basic supports are alkali supported on metal oxides, alkaline earth metal oxides, alkali and alkaline earth metal zeolites, transition metals, rare earths, and higher valence oxides: hydrotalcites, calcined hydrotalcites (mixed oxides, spinels), perovskite: beta-aluminas; metal hydroxides and carbonates: basic clays (limestone, dolomite, magnesite, sepiolite, olivine): metal nitrates, sulfides, carbides, phosphates, supported metal fluorides; activated and impregnated carbons; anionic exchange resins; organic bases supported on microporous or mesoporous metal oxides; solid or supported alkali and alkaline earth or organometallic metals;

After the Guerbet reaction step, the $C_6$ alcohol branched renewable formed, preferably 2,3-dimethyl-butanol (23DM-BuOH), is directed to a dewatering reactor.

The dewatering step is already known in the art. In one embodiment, the process of dehydrating alcohol to olefin preferably comprises a process containing two or more reactors with heating between the stages, or adding heated steam employing as catalysts, gamma-alumina or zeolites. It is also customary to employ steam in the reaction charge in order to limit the temperature decrease resulting from the endothermic reaction.

In a particular application, 2,3-dimethyl-1-butene can be recovered without hydrogenation to further obtain the renewable tetramethylethylene.

In one embodiment, the 2,3-dimethyl-1-butanol is converted to 2,3-dimethyl-1-butene, which is then directed to the hydrogenation step, also already known in the art.

Alternatively, the dewatering and hydrogenation reactions of 2,3-dimethyl-1-butanol can be effected in the same reactor, being performed on separate catalytic beds, passing the charge first into the dewatering catalyst and later into the hydrogenation catalyst. Another possibility is to mix the catalysts in the same reactor volume. Yet another possibility is an autothermal reactor, functioning as a heat exchanger, wherein the exothermic hydrogenation reaction provides heat to the endothermic dewatering reaction section.

A preferred scheme of the invention is to combine the dewatering functions with hydrogenation in a same catalyst. Examples of catalysts with both functions are hydrotreating catalysts, preferably chromium sulfides supported on alumina. In this configuration of combination of dewatering and hydrogenation the catalyst fulfills the so-called hydrodeoxygenation function. For this type of hydrotreating catalyst some amount of sulfur present in the charge may be required in the sulphated or EES form, continuously or intermittently.

The hydrogen required for hydrogenation can be fed prior to the hydrogenation step or fed prior to dewatering together with the charge.

The hydrogen can be fed "once through" or recycled maintaining a partial pressure of $H_2$ in the hydrogenation or hydrodeoxygenation reactor.

Typical dewatering conditions are temperatures between 100 and 500° C., preferably from 200 to 400° C.

Typical hydrogenation conditions depend on the nature of the catalyst used. In the case of a metal catalyst, reduced, such as Ni, Pt, Pd, Ru, typical temperature conditions are from 50 to 200° C. In the case of sulfided catalyst, from 200 to 400° C. The hydrogenation pressure is typically greater than 5 bar, preferably 10 to 80 bar, more preferably 20 to 60 bar.

Means for adding heat to the endothermic dewatering reaction, and removing heat generated in the exothermic hydrogenation reaction, are known in the art, and the heat generated in the hydrogenation is used to heat the dewatering step.

Many different types of reactors can promote dewatering and hydrogenation or hydrodeoxygenation reactions. One of them is the fixed bed reactor in packing flow with heterogeneous catalyst. These reactors are widely used in chemical and petrochemical processes.

Thus, in the embodiment described herein, the $C_6$ olefin, preferably 2,3-dimethyl-butene, is converted into high octane light isoparaffin of the present invention, preferably 2,3-dimethyl-butane.

The renewable origin of 2,3-dimethyl-butane can be proven using the analysis of isotopes of carbon.

Carbon is an element having 15 known isotopes, from $^8C$ to $^{22}C$. Of these isotopes, $^2C$ and $^{13}C$ are stable isotopes while others are unstable (radioisotopes) being degraded over time. Among the unstable carbon isotopes, $^{14}C$, which contain 6 protons and 8 neutrons, is the one having the longest life, with its half-life time (time required for the concentration of $^{14}C$ isotope to fall to half) equals to 5,700 years.

Although the isotope 14 of carbon is unstable, the effect of ambient radiation in the earth atmosphere causes its percentage in nature to remain approximately constant in the composition of carbonic in the atmosphere (about 1.1 parts per trillion) and consequently in living beings that metabolize this carbonic gas. In addition to living organisms, any product from these organisms, such as sugar, starch, cellulose, oils and derivatives thereof, maintain the same composition of $^{14}C$ of the atmosphere.

On the other hand, products from fossil-source feedstock, such as petroleum, coal and natural gas, do not exhibit $^{14}C$ in its composition. Fossil hydrocarbons are non-renewable resources because they take millions of years to form. Throughout this time of formation of fossil hydrocarbons, the decay of the isotope $^{14}C$ occurs in the composition of these products, since every 5,700 years the content of the isotope 14 of the carbon drops to half. This causes the final content of $^{14}C$ in fossil products to equal zero.

The methodology for measuring the carbon content is described in Technical Standards such as ASTM D6866 and revisions thereof, "*Standard Test Methods for Determining the Biobased Content of Solid. Liquid. and Gaseous Samples Using Radiocarbon Analysis*".

Additionally, the content of the isotope 14 of the carbon of products derived from renewable natural feedstocks remains constant throughout its processing.

Analysis of fractionated isoamyl alcohol from distillation of byproduct of sugar cane fermentation product has a carbon content of natural origin that equals 100% according to analysis of its carbon 14 content, according to ASTM D 6866 standard and revisions thereof.

When using methanol of fossil origin (that is, 0% renewable) with the isoamyl alcohol in the process of the present invention, the analysis of 2,3-dimethyl-butane points a carbon content of renewable natural origin of 83%, equivalent to 5/6 of the renewable carbon, from the isopropyl alcohol reactant.

When using as reactant methanol of renewable origin (100% renewable) from, but not limited to, for example, biomass gasification product, the 2,3-dimethyl-butane product reaches an index of 100% renewable carbon.

According to the present invention, the $C_6$ isoparaffin produced by the process described herein comprises at least 50% carbon of renewable natural origin in its composition, preferably from 80 to 100% of carbon of renewable origin in its composition.

The methanol used as reactant in present invention should be at least 50% renewable, preferably 100% renewable, in order to ensure a $C_6$ isoparaffin with 100% renewable carbon content. Furthermore, the compound produced by the claimed process has the following properties:
 octane RON/MON of 101 to 103.5/94.3
 Anti-Detonation Index (IAD) of 92 to 98, preferably 96;
 Reid Vapor Pressure (PVR) of 45 to 55 kPa, preferably 51.1 kPa.

The following are presented examples in order to illustrate various embodiments of the present invention without, however its contents.

EXEMPLOS

Exemplo 1: Reação Guerbet

For the tests in question the unit was loaded with Ni commercial catalyst on $MgO/Al_2O_3$ support. Such catalysts are typically used in pre-reforming reactions for hydrogen production. The catalyst, however, contains the two desired functions for the condensation reaction of the alcohols: the basic site of MgO and a hydrogenating/dehydrogenating function of Ni.

The pre-reduced and stabilized catalyst composition is 20% wt Ni, 5% wt NiO, 60% wt MgO and 15% wt $Al_2O_3$. It was reduced to 400° C. for 4 h.

The catalyst was comminuted in order to decrease its size but keeping the main dimension of mass transfer (6 mm) and then the intra particle strength equivalent to the industrial one.

A volume of 10 ml of catalyst was charged to the reactor, weighing 8.692 g, diluted in 10 ml of carborundum. The experiment was initiated by increasing the pressure, establishing H2 flow rate, starting heating to the desired temperature and thereafter establishing the charge flow rate (methanol+isoamyl alcohol). For experiments with addition of nitrogenated compound the charge was doped with equivalent to 1,500 ppm N in the charge.

Analytical results refer to the analysis of liquid effluent of each test, and only part of methyl ether (DME) produced by etherification of methanol remains dissolved in the product in the product collection conditions (ambient pressure and 20° C.).

GC/MS was used for analysis of the effluents from the reaction. Component gain factors for the FID detector, after identification, were calculated by the effective carbon number method, for component gain factor determination, relating the percentage to the gas chromatography area.

Table 1 shows the characteristics of the charge. The typical content of isopropyl alcohol (3-methyl-1-butanol) in the charge relative to 2-methyl-1-butanol is 80% of the first and 20% of the second. The contents of the total $C_5$ alcohols ($C_5OH$) are reported. Only 3-methyl-1-butanol reacts in the Guerbet reaction. The methanol content in the charge ranges from 35 to 70% wt in the molar ratios of 1.5 MeOH: 1 $C_5OH$ to 6 MeOH: 1 $C_5OH$.

TABLE 1

Property of charge for GC, FID

| Charge | % wt MeOH | % wt C5OH | % mol MeOH | % mol C5OH | Mol/mol MeOH/C5OH |
|---|---|---|---|---|---|
| 1.5 MeOH:1 | 35.5870 | 64.7130 | 60.0030 | 39.9970 | 1.5002 |
| 3 MeOH:1 $C_5OH$ | 52.1926 | 47.8074 | 75.0221 | 27.9979 | 3.0035 |
| 6 MeOH:1 $C_5OH$ | 67.0635 | 32.9365 | 84.8527 | 15.1473 | 5.6018 |

The operating conditions are listed in Table 2 and a summary of the main results in Table 3. It was chosen to start from a temperature greater than 350° C. as a function of chemical balances. The dehydrogenation reactions are most significantly favored from this temperature, which is evidenced by the results.

TABLE 2

Operating conditions of reaction:

| Test | Charge | doped N? | T, °C. | LHSV, hr$^{-1}$ | P, bar | H2/charge, NL/L |
|---|---|---|---|---|---|---|
| 1 | 1.5 MeOH:1 C5OH | No | 400 | 1 | 10 | 600 |
| 2 | 1.5 MeOH:1 C5OH | No | 400 | 1 | 10 | 600 |
| 3 | 1.5 MeOH:1 C5OH | No | 350 | 1 | 10 | 600 |
| 4 | 1.5 MeOH:1 C5OH | Yes | 350 | 1 | 10 | 600 |
| 5 | 1.5 MeOH:1 C5OH | Yes | 400 | 1 | 10 | 600 |
| 6 | 1.5 MeOH:1 C5OH | Yes | 450 | 1 | 10 | 600 |
| 7 | 1.5 MeOH:1 C5OH | Yes | 500 | 1 | 10 | 600 |
| 8 | 3 MeOH:1 C5OH | Yes | 400 | 0.5 | 10 | 1200 |
| 9 | 3 MeOH:1 C5OH | Yes | 400 | 0.25 | 10 | 2400 |
| 10 | 3 MeOH:1 C5OH | Yes | 400 | 2 | 10 | 600 |
| 11 | 3 MeOH:1 C5OH | Yes | 400 | 1 | 20 | 600 |
| 12 | 1.5 MeOH:1 C5OH | Yes | 400 | 2 | 10 | 600 |
| 13 | 6 MeOH:1 C5OH | Yes | 400 | 2 | 10 | 600 |
| 14 | 6 MeOH:1 C5OH | Yes | 400 | 4 | 10 | 600 |
| 15 | 6 MeOH:1 C5OH | Yes | 400 | 2 | 20 | 600 |
| 16 | 6 MeOH:1 C5OH:1 H2O | Yes | 400 | 2 | 20 | 600 |

TABLE 3

Main results in % wt

| | Products, % wt | | Ethers | | Aldehydes | | Olefins | | |
|---|---|---|---|---|---|---|---|---|---|
| Test | MeOH | C5OH | DME | MeOC5 | C5=O | C6=O | C5= | C6= | 23DM-BuOH |
| 1 | 6.2244 | 21.5769 | 0.1966 | 0.4611 | 6.2665 | 2.3124 | 56.4049 | 1.6241 | 4.2808 |
| 2 | 6.2557 | 21.8586 | 0.1932 | 0.4715 | 6.0691 | 2.3323 | 56.3195 | 1.6240 | 4.2234 |
| 3 | 22.2721 | 59.5448 | 0.2035 | 0.9675 | 5.6756 | 1.3530 | 3.8161 | 0.9051 | 5.1567 |
| 4 | 33.7051 | 53.1756 | 0.3851 | 0.9520 | 3.9115 | 1.0203 | 1.0771 | 0.3116 | 5.1070 |
| 5 | 12.6024 | 49.4943 | 0.6928 | 5.2406 | 5.4200 | 4.3778 | 3.4126 | 3.5943 | 13.9776 |
| 6 | 8.7647 | 31.7094 | 1.1355 | 7.7440 | 5.0023 | 7.9366 | 7.7644 | 6.9092 | 19.1497 |
| 7 | 7.6187 | 32.7742 | 0.2786 | 9.4702 | 5.0156 | 7.0873 | 11.3603 | 11.0318 | 10.7872 |
| 8 | 24.3344 | 36.5353 | 1.7100 | 7.2616 | 2.7489 | 3.8433 | 1.0954 | 2.3863 | 19.5556 |
| 9 | 26.8264 | 45.4372 | 2.0186 | 3.7612 | 2.2778 | 3.4527 | 0.2552 | 0.4880 | 14.8763 |
| 10 | 34.9841 | 34.5201 | 2.3245 | 3.7977 | 1.7645 | 2.2910 | 0.2287 | 0.5684 | 16.8834 |
| 11 | 30.5522 | 28.8403 | 4.3937 | 4.5402 | 1.2332 | 2.5206 | 0.6322 | 1.1894 | 22.5500 |
| 12 | 26.8264 | 45.4372 | 2.0186 | 3.7612 | 2.2778 | 1.9588 | 0.2552 | 0.4880 | 14.8763 |
| 13 | 44.6664 | 25.0560 | 3.4087 | 2.8933 | 1.1686 | 2.2082 | 0.3454 | 0.4972 | 17.1298 |
| 14 | 58.6052 | 22.2222 | 2.9440 | 1.6629 | 0.7439 | 1.1423 | 0.0000 | 0.1989 | 10.5676 |
| 15 | 52.4359 | 16.9596 | 4.3317 | 2.2795 | 0.5759 | 1.6347 | 0.1357 | 0.5913 | 18.0084 |
| 16 | 54.2356 | 18.5923 | 2.8977 | 1.5984 | 0.6294 | 1.6317 | 0.0779 | 0.4987 | 17.2599 |

Table 4 exhibits a summary of operating conditions and compositions of the reactants and major products and the mass ratio between the total of C6 and the sum of C5 and C6 in the product, C6/(C5+C6). This desired ratio from desired product to total of C5 and C6 compounds (alcohols, aldehydes, ethers, olefins and paraffins) is important to eliminate the dilution effect by MeOH or its loss, considering the actual effect of operating variables.

Tests 1 and 2 use the same conditions. The degree of dewatering of the alcohols and DME formation were high. The product exhibits a mass content of $C_5$ olefins, 56% wt, which means that most of $C_5OH$ dehydrated prior to dehydrogenating the aldehyde, as well as conversion of methanol into DME, not favoring the condensation of the alcohols. Although the catalyst has basic feature (MgO), there is still acidity in the remaining $Al_2O_3$ and metal sites, which has been found to be sufficient for dewatering.

The lower temperature in test 3, 350° C. showed lower dewatering, but even small yields of the condensation reaction producing 2,3-DMBuOH ($C_6OH$) in the product.

Thus, from the results shown, it is found that the addition of $NH_3$ precursor compound, of basic feature, could preferentially adsorb at sites of acid nature, minimizing the unwanted reactions such as dewatering and the formation of ethers such as methyl ether, providing more MeOH to be dehydrogenated and reacted with the isoamyl alcohol. It is emphasized that such a conclusion is an innovation in the art of using the condensation reaction of alcohols.

charge. Also increased the content of $C_5$ and $C_6$ olefin (this is being generated by dewatering of 2,3-DMBuOH, the main product of step), in similar contents. Furthermore, it is also increased the formation of ether product of the reaction between the $C_5$ ($C_5OH$) and MeOH, the $MeOC_5$. Aldehydes C5=O in the analysis appear almost invariant (right balance is most favored with temperature, but are consumed in condensation), while $C_6$-$C_{10}$ aldehydes increase with the

TABLE 4

Summary of operating conditions and yields expressed in % wt and ratios of $C_6$ and ether $MeOC_5$ per mass of $C_5 + C_6$

| Test | Charge | N? | Temp °C. | LHSV hr$^{-1}$ | wt % MeOH | wt % $C_5OH$ | Product, wt % MeOH | Product, wt % $C_5OH$ | 23DMBuOH ($C_6OH$) | C6/ (C5 + C6) | Ratio, % wt/ % wt, ether C5/(C5 + C6) |
|---|---|---|---|---|---|---|---|---|---|---|---|
| 1 | 1.5 | No | 400 | 1 | 35.29 | 64.71 | 6.22 | 21.58 | 4.28 | 0.0889 | 0.0050 |
| 2 | 1.5 | No | 400 | 1 | 35.29 | 64.71 | 6.26 | 21.86 | 4.22 | 0.0885 | 0.0051 |
| 3 | 1.5 | No | 350 | 1 | 35.29 | 64.71 | 22.27 | 59.54 | 5.16 | 0.0970 | 0.0127 |
| 4 | 1.5 | Yes | 350 | 1 | 35.29 | 64.71 | 33.71 | 53.18 | 5.11 | 0.0997 | 0.0147 |
| 5 | 1.5 | Yes | 400 | 1 | 35.29 | 64.71 | 12.60 | 49.49 | 13.98 | 0.2734 | 0.0653 |
| 6 | 1.5 | Yes | 450 | 1 | 35.29 | 64.71 | 8.76 | 31.71 | 19.15 | 0.4332 | 0.0987 |
| 7 | 1.5 | Yes | 500 | 1 | 35.29 | 64.71 | 7.62 | 32.77 | 10.79 | 0.3703 | 0.1213 |
| 8 | 3 | Yes | 400 | 0.5 | 52.19 | 47.81 | 24.33 | 36.54 | 19.56 | 0.3897 | 0.1097 |
| 9 | 3 | Yes | 400 | 0.25 | 52.19 | 47.81 | 26.83 | 45.44 | 14.88 | 0.2817 | 0.0563 |
| 10 | 3 | Yes | 400 | 2 | 52.19 | 47.81 | 34.98 | 34.52 | 16.88 | 0.3509 | 0.0675 |
| 11 | 3 | Yes | 400 | 1 | 52.19 | 47.81 | 30.55 | 28.84 | 22.55 | 0.4610 | 0.0797 |
| 12 | 1.5 | Yes | 400 | 2 | 35.29 | 64.71 | 26.83 | 45.44 | 14.88 | 0.2653 | 0.0576 |
| 13 | 6 | Yes | 400 | 2 | 67.06 | 32.94 | 44.67 | 25.06 | 17.13 | 0.4274 | 0.0623 |
| 14 | 6 | Yes | 400 | 4 | 67.06 | 32.94 | 58.61 | 22.22 | 10.57 | 0.3415 | 0.0477 |
| 15 | 6 | Yes | 400 | 2 | 67.06 | 32.94 | 52.44 | 16.96 | 18.01 | 0.5338 | 0.0601 |
| 16 | 6+ | Yes | 400 | 2 | 67.06 | 32.94 | 54.24 | 18.59 | 17.26 | 0.5012 | 0.413 |

Thus, from the results shown, it is found that the addition of $NH_3$ precursor compound of basic feature could preferentially adsorb at sites of acid nature, minimizing the unwanted reactions such as dewatering. It is emphasized that such a conclusion is an innovation in the art of using the condensation reaction of alcohols.

In fact, this result has been shown to be a success. From test 4, the addition of the nitrogenated compound decreased substantially the dewatering of MeOH and $C_5OH$ compounds, which only was found to be more significant from 450° C. (test 6)—but at much lower levels than without addition of the N. Thus, from the results shown, without limiting the claims of the invention to an interpretation of the results, it is assumed that the addition of $NH_3$ precursor compound, of basic feature, preferentially adsorbs at sites of acid nature, minimizing the unwanted reactions such as dewatering and the formation of ethers such as methyl ether, providing more MeOH to be dehydrogenated and reacted with the isoamyl alcohol. It is emphasized that such a conclusion is an innovation in the art of using the condensation reaction of alcohols.

The nitrogenates, n-propylamine, added generated $NH_3$ in the reaction conditions. Another possible reaction is $R-OH+NH_3$, resulting in $R-NH_2+2O$, heavier nitrogenates than the 2,3-DMBuOH. It is believed that adsorption will also occur in the acid sites. Small levels of heavier nitrogenates than 2,3-DMBuQH appeared in the chromatography (<0.1% of the area), and it is claimed its recirculation (as well as $NH_3$ in the vapor phase) to inhibit residual acidity of the catalyst improving selectivity thereof. Ammonia was detected in the reactor gas effluent.

Turning to Table 4, tests 4 through 7, varying the temperature and maintaining other conditions constant: up to 450° C. the yield of 2,3-DMBuOH in the product is increased, being converted the $C_5HOH$ and MeOH of the charge. Also temperature (balance effect and higher concentration of the precursor product 2,3-DMBuOH). Even the olefins generated are partially hydrogenated.

From the results of the tests presented, the following conclusions can be listed.

Effect of MeOH: $C_5OH$ ratio-Ratios tested 1.5:1, 3:1, and 6:1 molar. The object is to provide more reactant to force condensation with $C_5OH$. Higher ratios of MeOH led to greater amount of 2,3-DMBuOH but represent unreacted MeOH in the product that must be recovered for reuse in the reaction.

At the same temperature, the production of 2,3-DMBuOH increased, increasing C6/(C5+C6).
The undesirable side reactions decreased.
Probably the formation of $C_6$ olefins due to increase in competition with sites—the formation of $C_6$ olefins;
The formation of DME (MeOMe, methyl ether) decreased increasing the MeOH content in the product.
Increase in conversion of $C_5$=O aldehydes.
Decrease in formation of MeOCs ether.
Effect of pressure—pressures tested 10 and 20 bar.
higher pressure led to significant increase in the content of 2,3-DMBuOH obtained;
tests 8, 9 and 11: increase in conversion, even with greater LHSV in test 11.
Effect of LHSV—LHSV tested 4, 2, 1, 0.5, and 0.25 hr$^{-1}$.
Tests LHSV 0 and 0.25 had greater $H_2$/charge ratio than the others (tests 8 and 9) by experimental limitations, which apparently discourages dehydrogenation and conversion;
Tests 12 and 5: $C_6$ yield practically invariant, apparently near chemical balance was achieved with LHSV of 2 hr$^{-1}$.
Increasing LHSV from 2 to 4 h$^{-1}$ (tests 13 and 14) conversion decreased-likely it not reached balance condition in the greater LHSV Generally, the results teach that:

Temperatures above 500° C. are unnecessary: temperatures from 400° C. to 450° C. are preferred and temperatures below 350° C. insufficient for reaction- probably also related to chemical balance, besides the effect of the expected usual temperature.

LHSV of 1 to 2 hr$^{-1}$ preferred and LHSV of 4 hr$^{-1}$ extremely high;

differences between small LHSV, in practice LHSV 2 hr$^{-1}$, appear to be sufficient for near equilibrium condition.

Pressure increase helps the reaction (but is known to not favor dewatering).

Water decreases extraordinarily little the Guerbet reaction (test 16) but has a considerable effect in the decrease of etherification.

$C_6$ alcohol formed is 2,3-dimethyl-1-butanol.

Example 2: Hydrotreating Reaction

The combined product of the prior reactions was collected and combined in a same charge for the next hydrotreating step.

The reactor was charged with a hydrotreating catalyst, NiMO pre-sulfided supported in gamma-alumina.

The pressure was kept in 40 bar, ratio $H_2$/charge 600 ml/$H_2$ per ml pf charge. The reaction temperature was adjusted from 280 to 380° C. Analysis of the products showed mostly hydrocarbons in the product, like the proportions of charge, and that at 320° C. the total dewatering and hydrogenation of 2,3-dimethyl-butanol. It is understood from the results that acidity of the alumina of the support and the hydrogenating activity of the catalyst was sufficient to hydrogenate the aldehydes to alcohols, later dewatered and hydrogenated, as well as to hydrolyze the ethers in the presence of water from the reaction to alcohols, which in the sequence are also dewatered and hydrogenated.

Gas analysis of the high and product separator showed that some of the methanol is converted to methane, being preferable to remove the methanol prior to hydrogenation in order to avoid unnecessary consumption of hydrogen.

It is understood that the example refers to the combination of dewatering and hydrogenation reactions in a same HDT catalyst, being preferred the separation of the reactions in two separate catalysts.

The separation of 2,3-dimethyl-butane from the product and analysis of carbon 14 confirms the renewable origin.

Example 3: Additional Test of Guerbet Reaction

The test of Example 2 was repeated with higher pressures, 40 and 60 bar, obtaining higher yields in 2,3-dimethyl-butanol in the product.

The considerations and examples described herein demonstrate at least the following distinctive points of present invention over the prior art:

Obtaining renewable $C_6$ compounds from renewable $C_5$ compounds;

Guerbet reaction step between an initial charge of $C_5$ alcohol obtained from renewable raw material and methanol to produce a branched renewable $C_6$ alcohol;

Yield gains with the addition of ammonia or a nitrogenous compound in the Guerbet reaction between $C_5$ alcohol and methanol;

Use of isoparaffin with at least 50% carbon of renewable natural origin in high performance gasolines.

The invention claimed is:

1. A process for producing a high-octane renewable isoparaffin compound, comprising:
    a Guerbet reaction step between an initial charge of $C_5$ alcohol obtained from renewable raw material and methanol to produce a branched renewable $C_6$ alcohol;
    dewatering of the branched renewable $C_6$ alcohol to an $C_6$ olefin; and
    hydrogenation of the $C_6$ olefin to the high-octane renewable isoparaffin,
    wherein ammonia or a nitrogenous compound is added to the Guerbet reaction step between the $C_5$ alcohol and methanol.

2. The process of claim 1, wherein the methanol content in the initial charge is of 35 to 80% by weight and having a molar ratio for $C_5$ alcohol of 1.5:1 to 6:1.

3. The process of claim 1, wherein the $C_5$ alcohol is isoamyl alcohol comprising from 50 to 100% carbon of renewable natural origin.

4. The process of claim 3, wherein the isoamyl alcohol is from a fusel oil by-product of the sucrose fermentation from sugar cane.

5. The process of claim 1, wherein the methanol comprises 0 to 100% carbon of renewable natural origin.

6. The process of claim 1, wherein the branched renewable $C_6$ alcohol is 2,3-dimethyl-butanol and the $C_6$ olefin is 2,3-dimethyl-butene.

7. The process of claim 1, wherein the renewable isoparaffin is 2,3-dimethyl-butane comprising carbon of renewable natural origin.

8. The process of claim 1, wherein the ammonia or the nitrogenous compound is added in a content of 20 to 5,000 ppm.

9. The process of claim 1, wherein the nitrogenous compound is propylamine.

10. The process of claim 1, wherein the Guerbet reaction step occurs in a Guerbet reactor having:
    temperature from 250 to 550° C.;
    liquid hourly space velocity (LHSV) from 0.25 to 5 hr$^{-1}$;
    pressure from 1 to 100 bar;
    volume ratio $H_2$/charge from 10 to 2,000 NL/L.

11. The process of claim 10, further comprising a hydrogenation reactor after the Guerbet reactor having a temperature of less than 200° C., pressure between 5 and 60 bar, and liquid hourly space velocity (LHSV) between 1 and 5 hr$^{-1}$.

12. The process of claim 1, further comprising a separation section after the Guerbet reaction step to separate the branched renewable $C_6$ alcohol from at least one ether, methanol, and the $C_5$ alcohol.

13. The process of claim 12, wherein the at least one ether separated in the separation section undergo a hydrolysis step to be converted into methanol and the $C_5$ alcohol, wherein the converted methanol and the $C_5$ alcohol are recycled to the initial charge.

14. The process of claim 12, wherein the separation section comprises a water extraction and distillation process.

15. The process of claim 1, wherein a bifunctional catalyst having a basic site and a hydrogenating/dehydrogenating function is added to the Guerbet reaction step.

16. The process of claim 15, wherein the catalyst is Ni on a MgO/$Al_2O_3$ support, has from 10 to 30% wt Ni, 2 to 10% wt NiO, 50 to 70% wt MgO, and 5 to 25% wt $Al_2O_3$, and is reduced between 25° and 450° C.

17. The high-octane renewable isoparaffin compound produced by the process of claim 1, comprising at least 50% carbon of renewable natural origin.

18. The high-octane renewable isoparaffin compound of claim 17, wherein the carbon of renewable natural origin is 80 to 100%.

19. The high-octane renewable isoparaffin compound of claim 17, wherein the high-octane renewable isoparaffin compound is characterized by a research octane number (RON) of 101 to 103.5 and motor octane number (MON) of 94.3, an anti-detonation index (IAD) of 92 to 98, and a Reid vapor pressure (PVR) of 45 to 55 kPa.

20. A gasoline comprising the high-octane renewable isoparaffin compound produced by the process of claim 1.

* * * * *